United States Patent [19]

Kleemann et al.

[11] Patent Number: 4,482,760
[45] Date of Patent: Nov. 13, 1984

[54] PROCESS FOR THE PRODUCTION OF 1,2-DIOLS

[75] Inventors: Axel Kleemann, Hanau; Klaus Deller, Hainburg; Karlheinz Drauz, Freigericht; Bernd Lehmann, Constance, all of Fed. Rep. of Germany

[73] Assignee: Degussa Aktiengesellschaft, Frankfurt, Fed. Rep. of Germany

[21] Appl. No.: 552,106

[22] Filed: Nov. 16, 1983

[30] Foreign Application Priority Data

Nov. 19, 1982 [DE] Fed. Rep. of Germany ....... 3242749

[51] Int. Cl.³ .............................................. C07C 7/00
[52] U.S. Cl. .................................... 568/811; 568/814
[58] Field of Search ................................. 568/811, 814

[56] References Cited

U.S. PATENT DOCUMENTS 2,836,613  5/1958  Heininger ............................ 568/811
4,338,290  7/1982  Murib et al. ........................ 568/811

Primary Examiner—Werren B. Lone
Attorney, Agent, or Firm—Cushman, Darby & Cushman

[57] ABSTRACT

1,2-Diols of the formula:

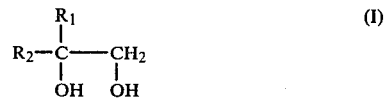

where $R_1$ and $R_2$ are hydrogen, alkyl of 1 to 10 carbon atoms or such as alkyl substituted by a halogen, a hydroxy group, a phenyl group, a methoxy group, or an ethoxy group, a phenyl group or a furyl group or $R_1$ and $R_2$ together form an alkylene group of 2 to 7 carbon atoms are formed by hydrogenating a correspondingly substituted cyanohydrin in an aqueous medium first in the presence of a hydrogenation catalyst and an acid at a temperature between $-20°$ and $+25°$ C. and a hydrogen pressure of less than 10 bar until per mole of cyanohydrin employed there is taken up one mole of hydrogen and then the hydrogenation continued to the end of the absorption of hydrogen in the presence of metallic nickel at a temperature between 30° and 100° C. and a hydrogen pressure between 10 and 150 bar.

22 Claims, No Drawings

PROCESS FOR THE PRODUCTION OF 1,2-DIOLS

SUMMARY OF THE INVENTION

The invention is directed to a process for the production of 1,2-diols of the general formula:

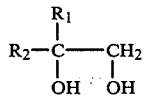

where $R_1$ and $R_2$ are the same or different and in each case can be hydrogen, a straight or branched chain, unsubstituted alkyl group of 1 to 10 carbon atoms or a 1 to 10 carbon atom alkyl group substituted by a halogen atom, a hydroxy group, a phenal group, a methoxy group, or an an ethoxy group, a phenyl group, or a furyl group or $R_1$ and $R_2$ together form a straight or branched chain alkylene group having 2 to 7 carbon atoms comprising hydrogenating a cyanohydrin of the formula:

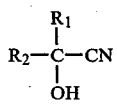

in which $R_1$ and $R_2$ are as defined above in an aqueous medium which per mole of cyanohydrin of formula (II) employed and contains at least 1 mole of water (a) in the presence of a palladium or platinum catalyst and, based on the cyanohydrin of general formula (II) at least one equivalent of an inorganic or organic acid or at least one equivalent of an acid ion exchanger, e.g. an acid ion exchange resin, or in the presence of metallic nickel and, again, based on the cyanohydrin equivalent of general formula (II), at least one equivalent of an acid ion exchanger at a temperature between $-20°$ and $+25°$ C. and a hydrogen pressure of less than 10 bar until one mole of hydrogen is taken up per mole of cyanohydrin of general formula (II) employed, and (b) continuing the hydrogenation in the presence of metallic nickel at a temperature between 30° and 100° C. and a hydrogen pressure between 10 and 150 bar until the end of the absorption of hydrogen.

The cyanohydrin of general formula (II) serving as starting materials for the process of the invention can be produced in the simplest manner according to known methods (see e.g. Houben-Weyl; Methoden der organischen Chemie, 4th edition, Georg Thieme Verlag, Stuttgart, Volume VIII, pages 274–278) from the corresponding aldehyde or ketone by reaction with hydrocyanic acid. Insofar as the production of the cyanohydrin is carried out in aqueous solution, these aqueous solutions can be employed directly for the process of the invention.

The aldehydes or ketones needed for the production of the cyanohydrins of general formula II for their part can, if necessary, also be produced in known manner (see, e.g, Houben-Weyl; Methoden der organischen Chemie, 4th edition, Georg Thieme Verlag, Stuttgart, Volume VII/1, pages 13–503 or Volume II/2a-c).

Examples of cyanohydrins of general formula II reacted according to the process of the invention includes propionaldehyde cyanohydrin, isobutyraldehyde cyanohydrin, valeraldehyde, cyanohydrin, hexanal cyanohydrin, heptanal cyanohydrin, octanal cyanohydrin, butanone cyanohydrin, pentanone cyanohydrin, methylisopropylketone cyanohydrin, diisopropylketone cyanohydrin, cyclohexanone cyanohydrin, 2-methylcyclohexanone cyanohydrin, 4-hydroxy-4-methylpentanone cyanohydrin, phenylacetaldehyde cyanohydrin, acetone cyanohydrin, phenylacetone cyanohydrin, 5-chloropentanone-2-cyanohydrin, methoxyacetaldehyde cyanohydrin, or mandelic acid nitrile. Additional cyanohydrins include 5-bromopentanone-2-cyanohydrin, 5-fluoropentanone-2-cyanohydrin, furylacetone cyanohydrin, furylacetaldehyde cyanohydrin, cyclopentanone cyanohydrin, ethoxyacetaldehyde cyanohydrin, dodecanal cyanohydrin and phenyl propionaldehyde cyanohydrin.

The process of the invention is especially suited for the conversion of glycolonitrile to ethylene glycol, lactic acid nitrile (acetaldehyde cyanohydrin) to 1,2-propanediol or n-butyraldehyde cyanohydrin to 1,2-pentanediol.

The cyanohydrins of general formula (II) are hydrogenated in a water containing medium which must contain at least 1 mole of water per mole of cyanohydrin employed. Insofar as the solubility of the cyanohydrin employed permits, water can be used as the sole solvent, otherwise there can also be employed as solvents mixtures of water with water soluble alcohols such as methanol, ethanol, n-propanol, isopropyl alcohol, n-butanol, isobutyl alcohol, secondary or tertiary butyl alcohol, dioxane or tetrahydrofuran. The solvent for example can be used in an amount between 0.5 and 100 ml, preferably between 1 and 50 ml, per gram of cyanohydrin employed.

In reaction step (A) the hydrogenation takes place in the presence of a palladium or platinum catalyst or in the presence of metallic nickel. Suitable catalysts for example are metallic palladium, especially as palladium black, metallic platinum, especially as platinum black, or platinum-IV oxide. If metallic palladium or platinum is used then it can be employed in the free form as well as the form of a catalyst on carrier using as the carrier for example activated carbon, barium sulfate, aluminum oxide or silica. Especially preferred catalysts are palladium black or palladium on activated carbon. The metallic nickel is preferably employed in the activated form of Raney-nickel. There can also be employed mixtures of several catalysts. The amount of catalyst employed is not critical to obtain short times, however, it is recommended to use the catalyst; calculated as active metal, in an amount between 0.1 and 100, preferably between 1 and 10 weight percent, based on the cyanohydrin of general formula (II).

In reaction step (a) furthermore, an acid is necessary. In using a palladium or platinum catalyst this can be an organic acid such as for example, formic acid, acetic acid or oxalic acid. However, there are preferably used mineral acids such as sulfuric acid, phosphoric acid and especially hydrochloric acid or an acid ion exchanger, e.g. an ion exchange resin such as a sulfonated styrene-divinyl benzene copolymer. The organic or inorganic acid is employed in the stoichiometric amount of one equivalent, based on the cyanohydrin employed of general formula (II). The use of an excess of acid is unsuitable. The acid ion exchanger must be employed in an amount of at least one equivalent based on the cyanohydrin employed of general formula (II). In this case, however, an excess is not disturbing. If nickel is used as the hydrogenation catalyst there is employed as the acid an acid ion exchanger in an amount of likewise at least one equivalent, based on the cyanohydrin employed of general formula (II).

The reaction step (a) is carried out at a temperature between −20° and +25° C., preferably between 0° and 20° C. and a hydrogen pressure of less than 10 bar, preferably between 1 and 2 bar. It is especially advantageous if there is led through the reaction mixture elemental hydrogen. After the taking up of one mole of hydrogen per mole of cyanohydrin of general formula (II) employed reaction step (a) is ended.

In the subsequent reaction step (b) the hydrogenation is carried out in the presence of metallic nickel, preferably in the activated form of Raney-nickel and under more severe conditions. Thereby it is not necessary to separate off the palladium or platinum catalysts and acid ion exchanger in a given case, in the reaction mixture. However, such separation can be suitable in order to make their recovery easier. If reaction step (a) is already carried out in the presence of metallic nickel, then generally the addition of further catalyst is not necessary. On the contrary, if reaction step (a) is carried out in the presence of a palladium or platinum catalyst, then there must be added metallic nickel. The suitable amounts of catalyst correspond to those given above for reaction step (a).

Reaction step (b) is carried out at a temperature between 30° and 100° C., preferably between 45° and 70° C. and at a hydrogen pressure between 10 and 150 bar, preferably between 14 and 40 bar.

Particularly high yields of 1,2-diols of general formula (I) are generally obtained if reaction (a) is carried out in the presence of palladium catalyst.

After the end of the taking up of hydrogen the catalysts and in a given case, ion exchanger contained in the reaction mixture are separated off, for example through filtration or centrifugation. Then from the remaining solution the 1,2-diol contained can be isolated in known manner, e.g. by fractional distillation or by extraction with a suitable organic solvent and subsequent fractional distillation.

The process can comprise, consist essentially of, or consist of the stated steps with the recited materials.

The invention is explained in more detail in the following examples. Unless otherwise indicated, all parts and percentages are by weight.

DETAILED DESCRIPTION

EXAMPLE 1

30.2 grams (0.5 mole) of glycolonitrile (94.3%) were dissolved in 150 ml of water and 300 ml of an acid ion exchanger added (sulfonated styrene-divinyl benzene resin).

After addition of 3.5 grams of a 10% Pd/activated carbon catalyst hydrogenation was carried out under stirring at 15° C. and a $H_2$ pressure of 2 bar until the taking up of 0.5 mole hydrogen. Then there were added 1.5 grams of an activated Ni catalyst, the temperature increased to 50° C. and the pressure to 15 bar and hydrogenation continued to the end of the $H_2$ take up (absorption). Then the catalysts and ion exchanger were filtered off. The solution was concentrated on a rotary evaporator and distilled.

The main part (26.2 grams) passed over at 196° to 198° C.

$n_D^{20} = 1.4310$, Yield of ethylene glycol: 84% of theory.

EXAMPLE 2

24.2 grams (0.4 mole) of glycolonitrile (94.3%) were dissolved in 200 ml of water and treated with 40 grams of concentrated HCl. After addition of 2.5 grams of a 10% Pd/activated carbon catalyst hydrogenration was carried out under stirring at 20° C. and 5 bar hydrogen pressure until a take up of 0.4 mole of hydrogen. Then there were added 2 grams of an activated nickel catalyst, the temperature increased to 30° C. and the hydrogen pressure to 15 bar and further hydrogenation continued until the end of the take up of hydrogen. Then the catalysts were filtered off. The solution was concentrated on a rotary evaporator and distilled. The main part (20.6 grams) passed over at 196° to 198° C.

$n_D^{20} = 1.4310$, Yield of ethylene glycol: 82.6% of theory.

EXAMPLE 3

40.0 grams (0.5 mole) of acetaldehyde cyanohydrin were dissolved in 200 ml of water and 300 ml of an acid ion exchanger (sulfonated styrene-divinyl benzene resin) added. After addition of 3.5 grams of a 10% Pd/activated carbon catalyst hydrogenation was carried out under stirring at 15° C. and a hydrogen pressure of 2 bar until the take up of 0.5 mole of hydrogen. Then there were added 1.5 grams of an activated nickel catalyst, the temperature increased to 50° C. and the pressure to 15 bar and hydrogenation continued until the end of the take up of the $H_2$. Then the catalyst and ion exchanger were filtered off. The solution was concentrated on the rotary evaporator and distilled.

The main part (28.1 grams) passed over at 16 mbar/84° C.

$n_D^{20} = 1.4320$, Yield 74% of theory of 1,2-propanediol.

EXAMPLE 4

35 grams (0.4 mol) of acetone cyanohydrin were dissolved in 250 ml of water and 250 ml of an acid ion exchanger (sulfonated sytrene-divinyl benzene resin) added. After addition of 3.5 grams of a 10% Pd/activated carbon catalyst hydrogenation was carried out with stirring at 15° C. and a $H_2$ pressure of 2 bar until take up of 0.5 mole of hydrogen. Then there were added 1.5 grams of an activated Ni catalyst, the temperature increased to 50° C. and the pressure to 15 bar and hydrogenation continued until the end of the $H_2$ take up. Then the catalysts and ion exchanger were filtered off. The solution was concentrated on the rotary evaporator and distilled.

The main part (29.3 grams) passed over at 16 mbar/79° C.

$n_D^{20} = 1.4360$, Yield of 2-methyl-1,2-propanediol: 81% of theory.

| Elemental analysis: | % C | % H |
|---|---|---|
| Calculated: | 53.31 | 11.19 |
| Found: | 53.23 | 11.02 |

EXAMPLE 5

42.0 grams (300 mmole) of mandelic acid nitrile were dissolved in 200 ml of water and 130 ml of ethanol and 150 ml of an acid ion-exchanger (Lewatit S100, sulfonated styrene-divinyl benzene resin) added. After addition of 4.0 grams of a 10% Pd/activated carbon catalyst hydrogenation was carried out under stirring at 15° C. and a H₂ pressure of 1.5 bar until takeup of 0.3 mole of H₂. Then there were added 2 grams of an activated Ni catalyst, the temperature increased to 45° C. and the pressure to 15 bar and hydrogenation continued until the end of hydrogen taken up. Then the catalysts and ion exchanger were filtered off. The reaction solution was concentrated on a rotary evaporator. The residue was colorless crystals which were recrystallized from ethanol.

Yield of 1-phenyl-1,2-ethanediol 25.1 grams, corresponding to 61% of theory. Melting Point: 65° C.

EXAMPLE 6

40.0 grams (0.4 mole) of butyraldehyde cyanohydrin were dissolved in 250 ml of water and 60 ml of ethanol and there were added 200 ml of an acid ion exchanger (Lewatit S100). After addition of 3 grams of a 10% Pd/activated carbon catalyst hydrogenation was carried out under stirring at 15° C. and a H₂ pressure of 1.2 bar until take up of 0.4 mole of hydrogen. Then there were added 3 grams of an activated nickel catalyst and the temperature increased to 50° C. and the hydrogen pressure to 15 bar and hydrogenation continued until the end of the hydrogen take up. Then the catalysts and ion exchanger were filtered off. The 1,2-pentanediol was separated off by distillation. The main part passed over at 53° to 55° C./0.06 mbar. Yield of 1,2-pentanediol: 31.17 grams, corresponding to 77% of theory.

EXAMPLE 7

50.0 grams (0.5 mole) of butyraldehyde cyanohydrin were dissolved in 100 ml of ethanol and 350 ml of water and 300 ml of an acid ion exchanger (Lewatit S100) added. After addition of 4 grams of an activated Ni catalyst hydrogenation was carried out under stirring at 15° C. and a hydrogen pressure of 1.2 bar until take up of 0.5 mole of hydrogen. Then the hydrogen pressure was increased to 15 bar and the temperature to 50° C. and hydrogenation continued until the end of the hydrogen taken up. The catalyst and ion exchanger were filtered off. The solution was concentrated on a rotary evaporator, then distilled. The main part passed over at 53° to 55° C. and 0.06 mbar. Yield of 1,2-pentanediol: 35.5 grams, corresponding to 68.2% of theory.

EXAMPLE 8

24.8 grams (0.25 mole) of butyraldehyde cyanohydrin were dissolved in 180 ml of water and 20 ml of ethanol and treated with 25 grams of HCl. After addition of 1.25 grams of a 10% Pd/activated carbon catalyst hydrogenation was carried out with stirring at 25° C. and 9 bar hydrogen pressure until take up of 0.25 mole of hydrogen. Then there were added 2.0 grams of an activated Ni catalyst, the temperature increased to 35° C. and the hydrogen pressure increased to 20 bar and hydrogenation continued until the end of hydrogen take up. The solution was concentrated on a rotary evaporator and distilled. The main portion (19.1 grams) passed over at 53° to 55° C./0.06 mbar. Yield of 1,2-pentanediol: 73.3% of theory.

EXAMPLE 9

Example 8 was repeated with the sole difference that in place of concentrated HCl there were employed 13 grams of H₂SO₄. The yield of 1,2-pentanediol: 73% of theory.

EXAMPLE 10

Example 8 was repeated with the sole difference that in place of concentrated HCl there were employed 15 grams of glacial acetic acid. Yield of 1,2-pentanediol: 70% of theory.

EXAMPLE 11

Example 8 was repeated with the sole difference that in place of Pd/activated carbon catalyst there was employed a 10% Pt/activated carbon catalyst. Yield of 1,2-pentanediol: 65% of theory.

EXAMPLE 12

Example 8 was repeated with the sole difference that in place of Pd/activated carbon catalyst there was employed Pd black. Yield of 1,2-pentanediol: 72% of theory.

EXAMPLE 13

Example 8 was repeated with the sole difference that in place of Pd/activated carbon catalyst there was employed a 10% Pd/BaSO₄ catalyst. Yield of 1,2-pentanediol: 75% of theory.

EXAMPLE 14

Example 8 was repeated with the sole difference that in place of Pd/activated carbon catalyst there was employed a 10% Pd/SiO₂ catalyst. Yield of 1,2-pentanediol: 71% of theory.

The entire disclosure of German priority application P No. 3242749.2 is hereby incorporated by reference.

What is claimed is:

1. A process for the production of a 1,2-diol of the general formula

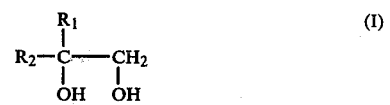

where each of R₁ and R₂ is hydrogen, an alkyl group of 1 to 10 carbon atoms or a 1 to 10 carbon atom alkyl group substituted by a halogen atom, a hydroxy group, a phenyl group a methoxy group, or an ethoxy group, a phenyl group or a furyl group or R₁ and R₂ together form an alkylene group having 2 to 7 carbon atoms comprising hydrogenating a cyanohydrin of the formula

in an aqueous medium which per mole of cyanohydrin of formula (II) employed contains at least 1 mole of water, (a) in the presence of a palladium or platinum catalyst and, based on the cyanohydrin of formula (II) at least one equivalent of an inorganic or organic acid or at least one equivalent of an acid ion exchanger or in the presence of metallic nickel and, again based on the cyanohydrin of formula (II), at least one equivalent of an acid ion exchanger at a temperature between −20° and +25° C. and a hydrogen pressure of less than 10 bar until one mole of hydrogen is taken up per mole of cyanohydrin of formula (II) employed, and (b) continuing the hydrogenation in the presence of metallic nickel at a temperature between 30° and 100° C. and a hydrogen pressure between 10 and 150 bar until the end of the absorption of hydrogen.

2. A process according to claim 1 where $R_1$ is hydrogen or alkyl of 1 to 10 carbon atoms and $R_2$ is hydrogen, alkyl of 1 to 10 carbon or phenyl.

3. A process according to claim 2 where $R_2$ is phenyl.

4. A process according to claim 2 where $R_2$ is hydrogen.

5. A process according to claim 2 where the compound of formula (II) is glycolonitrile, acetaldehyde cyanohydrin, acetone cyanohydrin, mandelic acid nitrile, or butryaldehyde cyanohydrin.

6. A process according to claim 1 wherein reaction step (a) is carried out with a palladium or platinum catalyst.

7. A process according to claim 6 wherein reaction step (a) is carried out in the presence of hydrochloric acid.

8. A process according to claim 7 wherein reaction step (a) is carried out at a temperature between 0° and 20° C.

9. A process according to claim 1 wherein reaction step (a) is carried out at a temperature between 0° and 20° C.

10. A process according to claim 9 wherein reaction step (a) is carried out at a hydrogen pressure between 1 and 2 bar.

11. A process according to claim 1 wherein reaction step (a) is carried out at a hydrogen pressure between 1 and 2 bar.

12. A process according to claim 8 wherein reaction step (a) is carried out at a hydrogen pressure between 1 and 2 bar.

13. A process according to claim 7 wherein reaction step (a) is carried out at a hydrogen pressure between 1 and 2 bar.

14. A process according to claim 12 wherein reaction step (b) is carried out at a temperature between 45° and 70° C.

15. A process according to claim 11 wherein reaction step (b) is carried out at a temperature between 45° and 70° C.

16. A process according to claim 10 wherein reaction step (b) is carried out at a temperature between 45° and 70° C.

17. A process according to claim 1 wherein reaction step (b) is carried out at a temperature between 45° and 70° C.

18. A process according to claim 17 wherein reaction step (b) is carried out at a hydrogen pressure between 15 and 20 bar.

19. A process according to claim 16 wherein reaction step (b) is carried out at a hydrogen pressure between 15 and 50 bar.

20. A process according to claim 15 wherein reaction step (b) is carried out at a hydrogen pressure between 15 and 50 bar.

21. A process according to claim 1 wherein reaction step (b) is carried out at a hydrogen pressure between 15 and 50 bar.

22. A process according to claim 1 wherein steps (a) and (b) are carried out in water or a mixture of water and a water soluble alcohol, dioxane, or tetrahydrofuran.

* * * * *